United States Patent [19]
Novotny

[11]   4,255,594
[45]   Mar. 10, 1981

[54] HYDROGENATION OF HALOGEN-CONTAINING CARBOXYLIC ANHYDRIDES

[75] Inventor: Miroslav Novotny, Denville, N.J.

[73] Assignee: Allied Chemical Corporation, Morris Township, Morris County, N.J.

[21] Appl. No.: 76,658

[22] Filed: Sep. 18, 1979

[51] Int. Cl.$^3$ .............................................. C07C 31/38
[52] U.S. Cl. ................................................... 568/842
[58] Field of Search .......................................... 568/842

[56] References Cited

U.S. PATENT DOCUMENTS

| | | | |
|---|---|---|---|
| 3,314,987 | 4/1967 | Case et al. | 568/842 |
| 3,356,746 | 12/1967 | Anello et al. | 568/842 |
| 3,356,746 | 12/1967 | Anello et al. | 568/842 |
| 4,072,726 | 2/1978 | Nychka et al. | 568/842 |

FOREIGN PATENT DOCUMENTS 514803  5/1978  U.S.S.R. ................................... 568/842

OTHER PUBLICATIONS

Swart, "Compt. Rend" 197 1261 (1933).

Chem Abstract, vol. 28, pp. 1987, Swarts.

*Primary Examiner*—Werren B. Lone
*Attorney, Agent, or Firm*—Robert A. Harman

[57]   ABSTRACT

A process is described for the heterogeneous hydrogenation of haloalkyl, halocycloalkyl or haloaryl carboxylic anhydrides to the corresponding primary alcohols. In the haloalkyl or halocycloalkyl carboxylic anhydrides at least one halogen is in the alpha-position relative to the carboxylic anhydride grouping. The hydrogenation can be carried out in the liquid or vapor phase in the presence of a supported or unsupported catalyst comprising a member of the group consisting of rhodium, iridium, metal oxides thereof, or mixtures thereof. In the liquid phase, the hydrogenation can be carried out batchwise under mild conditions of temperature and pressure, preferably at about 50°–150° C. and about 5–15 atmospheres, in an atmosphere containing hydrogen gas. A preferred embodiment is the hydrogenation of trifluoroacetic anhydride in the liquid phase to 2,2,2-trifluoroethanol, said alcohol being useful as an intermediate in the synthesis of the anesthetic, isoflurane, $CF_3CHClOCHF_2$.

5 Claims, No Drawings

HYDROGENATION OF HALOGEN-CONTAINING CARBOXYLIC ANHYDRIDES

BACKGROUND OF THE INVENTION

This invention relates to a process for hydrogenating haloalkyl, halocycloalkyl or haloarylcarboxylic anhydrides to primary alcohols, in the liquid or vapor phase, in the presence of a solid rhodium or iridium catalyst, supported or unsupported, employed as the metal, metal oxide, or mixtures thereof.

Fluorine-containing alcohols are useful as solvents for a wide variety of organic compounds and are also useful as reagents for producing fluorine-containing esters of carboxylic acids, in which the alcohol moiety contains fluorine substituents. A commercially important fluorine-containing alcohol is 2,2,2-trifluoroethanol which can be used to produce the known anesthetic, isoflurane, $CF_3CHClOCHF_2$.

Methods for producing fluorine-containing alcohols, such as 2,2,2-trifluoroethanol, usually involve the reduction of esters containing this alcohol moiety. For example, U.S. Pat. Nos. 3,314,987 and 4,072,726 (to Allied Chemical Corporation) describe the hydrogenation of such fluorine-containing esters over a copper oxide-based catalyst to produce fluorine-containing alcohols and similarly, U.S. Pat. No. 3,356,746 (to Allied Chemical Corporation) describes the hydrogenation of fluorine-containing esters over supported and unsupported ruthenium and palladium catalysts.

However, processes for hydrogenating halogen-containing alkyl carboxylic anhydrides directly to the corresponding primary alcohols are not well known since these anhydrides are generally more resistant to reduction than are the esters. This is particularly true for the lower members of the class such as trifluoroacetic anhydride and perfluoropropionic anhydride.

Anhydrides usually survive most catalytic hydrogenations. Prolonged, or vigorous reductions, however, may lead to hemiacetals, esters, acids, alcohols or even to hydrocarbons.

$(RCO)_2O + H_2 \rightarrow (RCHOH)OCOR$
$(RCHOH)OCOR + H_2 \rightarrow RHC_2OH + RCOOH$

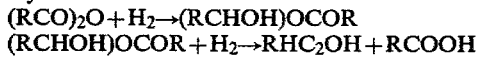

$RCH_2OH + H_2 \rightarrow RCH_3 + H_2O$
$RCOOH + 2H_2 \rightarrow RCH_2OH + H_2O$

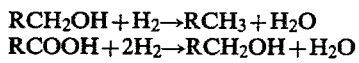

F. Swartz in Compt. Rend. 197, 1261 (1933) discloses reduction of trifluoroacetic anhydride in the liquid phase over platinum black at 20°-40° C. and 45-50 atm. Principal products of the reduction were $CF_3CH_2OCOCF_3$, $CF_3CH_2OH$ and $CF_3CH_3$.

Zabolotskih et al. in USSR Pat. No. 514,803 issued May 1978 disclose vapor phase reduction of trifluoroacetic anhydride over a supported Pt or Ni catalyst resulting in predominant production of $CF_3CH_2OH$.

No mention is made in the above-described references of the use of rhodium or iridium-based catalysts for the heterogeneous hydrogenation of halogen-containing carboxylic anhydrides to a corresponding primary alcohol group.

Since the preparation of fluorine-containing alcohols by the direct hydrogenation of the corresponding fluorine-containing carboxylic anhydrides is potentially commercially attractive, what is desired is a direct one-step hydrogenation process applicable to a large class of fluorine-containing carboxylic anhydrides proceeding at reasonable rate under mild conditions of temperature and pressure.

SUMMARY OF THE INVENTION

In accordance with this invention, there is provided a process for hydrogenating haloalkyl, halocycloalkyl or haloaryl carboxylic anhydrides, with the proviso that in such haloalkyl or halocycloalkyl group at least one halogen is in alpha position relative to the carboxylic anhydride grouping, to primary alcohols comprising the step of contacting said anhydride in the liquid or vapor phase with an atmosphere containing hydrogen gas in the presence of a supported or unsupported solid rhodium or iridium catalyst, employed as the metal, the metal oxide, or mixtures thereof.

A feature of the invention process is the surprising discovery of the use of solid supported or unsupported rhodium or iridium catalysts, employed as the metal, the metal oxide or mixture thereof, such as rhodium on carbon, rhodium on alumina, rhodium oxide hydrate, rhodium black, iridium black, or mixtures thereof, which allow the hydrogenation to be conducted under mild conditions of temperature and pressure.

Advantages of the invention process include the high yield hydrogenation of fluorine-containing $C_2$-$C_3$ alkyl carboxylic anhydrides, particularly trifluoroacetic anhydride, at low temperture and low pressure, rendering the process extremely attractive from a commercial standpoint.

By the term "hydrogenation", as used herein is meant the reduction of a carboxy group in halogen-containing carboxylic anhydrides to the primary alcohols wherein hydrogen is the active reducing agent. Also, by the term "contacting" as used herein, is meant the physical interaction of the atmosphere, containing hydrogen gas, with the reaction mixture of fluorine-containing carboxylic anhydride and solid catalyst.

DETAILED DESCRIPTION OF THE INVENTION AND PREFERRED EMBODIMENTS

REACTION EQUATION AND STARTING MATERIALS

In one aspect, the invention process can be represented by the following equation:

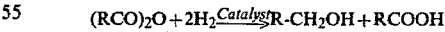

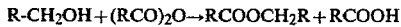

wherein R is independently hydrogen, a haloalkyl, a halocycloalkyl, or a haloaryl group, said haloalkyl group being linear or branched and said halocycloalkyl and haloaryl groups being substituted or unsubstituted, with the proviso that in such anhydride not more than one R is hydrogen and that in such haloalkyl or halocycloalkyl group at least one halogen is in alpha-position relative to the carboxylic anhydride grouping. By haloaryl group is meant an aryl group having a halogen substituent on the ring attached to the carboxylic anhydride grouping. Said haloalkyl, halocycloalkyl or haloaryl groups can also contain substituents including C$_1$-C$_4$ linear or branched alkyl or C$_1$-C$_4$ linear or branched alkoxy substituents, and the like, which are non-interfering under the reaction conditions.

The scope of haloalkyl, halocycloalkyl, or haloaryl carboxylic anhydrides applicable in the invention process, having the above formula as defined for R, includes those alkyl, cycloalkyl and aryl derived carboxylic anhydrides containing at least one carbon-halogen bond, 2 to 24 carbon atoms, and at least one carboxylic anhydride grouping in the molecule. The anhydrides include compositions having the formula (R'$_n$CX$_{3-n}$CO)$_2$O, (R'$_n$CX$_{3-n}$CO)O(OCH),
([C$_6$R'$_m$X$_{5-m}$]CO)$_2$O, ([C$_6$R'$_m$X$_{5-m}$]CO)O(OCH),
([C$_6$R'$_m$X$_{5-m}$]CO)O(R'$_n$CX$_{3-n}$CO)

and mixtures thereof wherein n=0, 1, 2; m=0, 1, 2, 3, 4; X is independently fluorine, chlorine, bromine or iodine; and R' is independently hydrogen, alkyl, haloalkyl, alkoxyalkyl, cycloalkyl, halocycloalkyl, alkoxycycloalkyl, aryl, haloaryl or alkoxyaryl, having up to about 20 carbon atoms. Examples of carboxylic anhydrides applicable in the invention process include monofluoroacetic anhydride, difluoroacetic anhydride, monoiodoacetic anhydride, monobromoacetic anhydride, monochloroacetic anhydride, monofluoroacetic anhydride 2-fluoropropionic anhydride, 2-fluorosuccinic anhydride, 2-fluoromaleic anhydride, 2-fluoroisobutyric anhydride, 2-fluoro-n-butyric anhydride, 2-fluoro-n-valeric anhydride, 2-fluorostearic anhydride, 2-fluorocaproic anhydride, 2-fluoro-n-heptylic anhydride, 2-fluorocaprylic anhydride, 2-fluoropelargonic anhydride, 2-chloropropionic anhydride, 2-bromoglutonic anhydride, 2-chloroadipic anhydide, 2-fluoropimelic anhydride, 2-fluorosebacic anhydride, 2-fluoroazelaic anhydride, 2-fluoroundecanedioic anhydride, 2-fluorododecanedioic anhydride, dichloroacetic anhydride, trichloroacetic anhydride, 2-fluorobenzoic anhydride, 3-fluorophthalic anhydride, 2-phenyl-2,2-difluoroacetic anhydride, trifluoroacetic anhydride, 2,2-difluoropropionic anhydride, perfluoropropionic anhydride, heptafluorobutyric anhydride, perfluoroisobutyric anhydride, perfluorovaleric anhydride, perfluorohexanoic anhydride, perfluoroheptanoic anhydride, perfluorooctanoic anhydride, perfluorononanoic anhydride, perfluorodecanoic anhydride, perfluorocyclohexane carboxylic anhydride, perfluorocyclohexyl acetic anhydride, pentafluorobenzoic anhydride, and 2,4-difluorobenzoic anhydride.

Mixed anhydrides include monofluoroacetic-formic-anhydride, 2-fluoropropionic-formic-anhydride, and p-fluorobenzylic-formic-anhydride.

Preferred carboxylic anhydrides in the invention process are those that are perfluorinated. Also preferred are haloalkyl carboxylic anhydrides containing 2–10 carbon atoms. More preferred are linear alkyl carboxylic anhydrides containing 2–4 carbon atoms and a particularly preferred anhydride in the process is trifluoroacetic anhydride. By the term "anhydride", as used herein, is meant the halogen-containing carboxylic anhydride as described above.

As is seen in the above equation, the stoichiometry of the hydrogenation reaction requires at least two moles of elemental hydrogen per mole of halogen-containing carboxylic anhydride. Under the reaction conditions the produced ester and the acid can be further reduced to the primary alcohol. The overall yield is two moles of the alcohol per mole of the anhydride with the consumption of four moles of hydrogen:

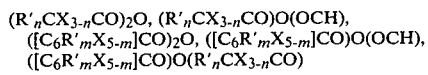

Halogen for the purposes of this invention means fluorine, chlorine, bromine, iodine and their mixtures, with fluorine and chlorine preferred and fluorine more preferred.

PROCESS CATALYST

A novelty in the process is the use of a supported or unsupported catalyst comprising a member of the group consisting of metallic rhodium, iridium, metal oxides thereof, or mixtures thereof, which allows the hydrogenation of alpha-halocarboxylic anhydrides to be conducted under mild conditions. The reason why these particular catalysts are surprisingly effective in the hydrogenation of fluorine-containing carboxylic anhydrides is not known. Said catalyst is a solid under the reaction conditions, and can be suspended in the liquid anhydride neat or in dispersion or solution during a liquid phase process, or suspended as a fixed or fluidized bed during a continuous vapor phase process. Thus, the solid catalyst acts as a heterogeneous catalyst under the reaction conditions. Representative examples of unsupported catalysts include metallic rhodium, rhodium black, metallic iridium, iridium black, rhodium oxide and iridium oxide. Also included are rhodium and iridium chloride and rhodium and iridium complexes which decompose under the reaction conditions to the corresponding metals or metal oxides. By the term "black" is meant a finely divided metal. The catalyst, may also be supported on suitable substrates including carbon, alumina, silica, and other high surface area carriers. Preferred supports are carbon, being activated carbon, and alumina. Representative examples of catalysts supported on various substrates are rhodium on carbon, rhodium on alumina, iridium on carbon, iridium on alumina, rhodium oxide on carbon, rhodium oxide on alumina, iridium oxide on carbon, iridium oxide on alumina, rhodium on silica, rhodium oxide on silica, iridium on silica and iridium oxide on silica. Preferred catalysts are selected from the group consisting of from about 2 to 10 weight percent rhodium on carbon, from about 2 to 10 weight percent rhodium on alumina, rhodium black, iridium black, rhodium oxide hydrate, or mixtures thereof. A particularly preferred catalyst is about 5 weight percent rhodium on carbon, also designated herein as 5% Rh/C. The catalysts useful in the invention process may be prepared by conventional methods or obtained commercially.

The amount of total catalyst present in the process, and by the term "total catalyst" is meant active catalyst material including support if present, is not critical for operability and may be from about 0.001 to 20 weight percent of said anhydride present in either the liquid or vapor phase. A preferred amount is about 5 weight percent total catalyst present of the weight of said anhydride present.

GENERAL PROCESS CONDITIONS

The process can be conducted in the liquid or vapor phase. In the liquid phase, the anhydride can be present in neat form, above its melting point, or dispersed in a liquid or dissolved in a suitable solvent. Such dispersing liquid or solvent, if used, should be inert under the reaction conditions. A solvent if used, should possess adequate solvating ability for the anhydride, be a non-solvent for the catalyst and provide a solution of the anhydride below the decomposition temperature of said anhydride. Representative classes of solvents applicable in the process include fluorine-containing esters, non-fluorine-containing carboxylic acids, anhydrides and hydrocarbons. A preferred class of solvents are fluorine-containing esters including ethyl trifluoroacetate and trifluoroethyl trifluoroacetate. The amount of solvent, if used, can be about 0.1 to 10 parts by weight per part of said anhydride. However this amount is not critical, lower and higher amounts being also effective with the proviso that sufficient solvent is present to dissolve said anhydride to initiate and maintain the hydrogenation reaction.

The process can also be conducted in the vapor phase, in which a dispersion of said carboxylic anhydride at or above its boiling point, in a stream of other vapors or gases including hydrogen gas, is contacted with the catalyst described herein, preferably in a continuous manner.

The process in the liquid phase may be conducted as a simple batch reaction, or as a series of batch reactions in a continuous manner, in which the liquid product mixture is removed from the reaction vessel, such as by decantation or distillation, and a fresh charge of said anhydride added to the reactor to repeat the reaction process.

The process in the vapor phase can be conducted, preferably in a continuous manner, by contacting a stream of anhydride, above its boiling point, and hydrogen gas with the solid catalyst described herein forming a fixed or fluidized bed.

REACTION CONDITIONS

For effective hydrogenation in the liquid phase, the catalyst should be suspended throughout the liquid anhydride media during the hydrogenation to insure maximum contact of catalyst surface with the anhydride. This is generally accomplished by agitation, or continuous stirring of the reaction contents during the process.

The temperature in the liquid or vapor phase process must be below the decomposition or decarboxylation temperature of the anhydride being hydrogenated. In the liquid phase process, the temperature must also be at about, or below, the boiling point of said anhydride, and above the melting point of said anhydride, under the reaction conditions, such that a substantial amount of anhydride is present as a liquid. The process temperature range includes the range of about 50°–200° C., and preferably about 50°–150° C. The temperature range in the vapor phase embodiment is generally above the boiling point of said anhydride.

Pressure in the process may be from 1 to 500 atmospheres. Higher pressures than 500 atmospheres, being the upper safety limit of known commercial pressure apparatus, may also be used, as well as lower pressures than one atmosphere provided sufficient hydrogen gas is present to initiate and maintain the hydrogenation reaction. From a commercial standpoint, milder conditions are very desirable and for this reason, pressures of about 5 to about 15 atmospheres are preferred in the process reaction.

The atmosphere with which the anhydride, being in the liquid or vapor phase, is in contact during the process contains hydrogen gas. Other inert gases such as argon, nitrogen, may also be present in said atmosphere as long as sufficient hydrogen gas is present to initiate and maintain the hydrogenation reaction. This amount is generally about 4 moles of hydrogen gas per mole of anhydride desired to be hydrogenated. Usually a slight excess of about 20 mole percent of hydrogen gas above the stoichiometric quantity is utilized to insure high yields in the process. Preferably, the atmosphere contacting the anhydride during the process consists essentially of hydrogen gas.

Length of time for conducting the process either in the liquid or vapor phase will depend upon the particular anhydride, catalyst, temperature, pressure employed, and the like. In general, reaction times of about 2–24 hours will produce satisfactory yields of product alcohol in the liquid phase process. Contact times of about 1 to 10 seconds will produce satisfactory yields of product alcohol in a continuous vapor phase process. In the preferred embodiment, where trifluoroacetic anhydride is hydrogenated in the liquid phase, in the presence of about 5% rhodium on carbon, at a temperature of about 50°–150° C. and a pressure of about 5–15 atmospheres, in an atmosphere consisting essentially of hydrogen gas, reaction times of about 2–6 hours will generally produce product 2,2,2-trifluoroethanol in yields of about 75% of theory.

The product alcohol can be isolated from the reaction mixture obtained in either the liquid or vapor phase process by conventional methods such as fractional distillation, column and gas chromatography and the like. Purification of the obtained alcohol can also be accomplished by the above-described conventional methods and the like. Methods for isolating and purifying the product alcohol will be obvious to one skilled in the art.

Yields of halogen-containing alcohol in the process, based on the starting amount of halogen-containing carboxylic anhydride, are as high as 75% of theory.

REACTION APPARATUS

Apparatus for carrying out the invention process in the liquid phase can be any conventional type of glass or metal pressure reactor apparatus equipped with means for heating and stirring the reaction contents during the reaction, means for observing and monitoring the reaction pressure, means for introducing the reactants and means for recovering products and spent catalyst. Apparatus for carrying out the process in the vapor phase in a continuous manner can be any conventional continuous fixed bed or fluidized bed apparatus with means for mixing a stream of vaporized anhydride and hydrogen gas and contacting the composite stream with the catalyst described herein for a predetermined contact time interval. Apparatus for conducting the invention process will be obvious to one skilled in the art from this disclosure.

REACTION PRODUCTS

The hydrogenation of a carboxy group in the halogen-containing carboxylic anhydrides in the process results in the 1,1-dihydro primary alcohols and their esters as illustrated in the above equations in which the carbon, to which the primary alcohol group is attached, is halogen free. Other functional groups or radicals contained in the anhydride may be present and may be concomitantly hydrogenated under the reaction process conditions. However, such groups or radicals are not required in the invention process. The term "2-halo" as applied to said alcohol herein, means that said alcohol has a halogen at the carbon atom next to the carbon with the hydroxy group. Representative examples of halogen-containing alcohols produced in the invention process are 2-fluoroethanol; 2,2-difluoroethanol; 2-iodoethanol, 2-bromoethanol, 2-chloroethanol, 2-fluoropropanol, 2-fluoroisobutyanol, 2-fluoro-n-butanol, 2-fluorohexanol, 2fluoro-n-heptanol, 2-fluorooctanol, 2-fluorononanol, 2-chloropropanol, 2-chlorohexandiol-1,6, 2,2-chloroethanol, 2,2,2-trichloroethanol, 2-fluorobenzyl alcohol, 2-phenyl-2,2-difluoroethanol; 2,2,2-trifluoroethanol; 2,2-difluoro-n-propyl alcohol; 3,3,3,2,2-pentafluoro-n-propyl alcohol; 4,4,4,3,3,2,2-heptafluoro-n-butanol; 2,2-di(trifluoromethyl)-2-fluoroethanol; 5,5,5,4,4,3,3,2,2-nonafluoro-n-pentanol; 6,6,6,5,5,4,4,3,3,2,2-undecafluoro-n-hexanol; 7,7,7,6,6,5,5,4,4,3,3,2,2-tridecafluoro-n-heptanol; 8,8,8,7,7,6,6,5,5,4,4,3,3,2,2-pentadecafluoro-n-octanol; 9,9,9,8,8,7,7,6,6,5,5,4,4,3,3,2,2-heptadecafluoro-n-nonanol; 10,10,10,9,9,8,8,7,7,6,6,5,5,4,4,3,3,2,2-nonadecafluoro-n-decanol; 1,2,2,3,3,4,4,5,5,6,6-undecafluorocyclohexylmethanol; 2-(1,2,2,3,3,4,4,5,5,6,6-undecafluoro)-cyclohexyl-2,2-difluoroethanol; 1,2,3,4,5-pentafluorobenzyl alcohol; and 2,4-difluorobenzyl alcohol. A preferred product alcohol in the process is 2,2,2-trifluoroethanol.

PREFERRED MODES OF THE PROCESS

It is preferred during the liquid phase process to initially charge the catalyst and anhydride into the reactor and degasify the mixture, for example, such as by first freezing the mixture and then subjecting the contents to a vacuum to remove gases in the anhydride and absorbed gases off from the surface of the catalyst. The mixture is then allowed to thaw to liquefy, hydrogen gas is introduced and the reaction is carried out. Other techniques for activating the catalyst surface can also be used and will be obvious to one skilled in the art. The progress of the reaction process can be monitored by a conventional pressure gauge or manometer and the process is continued until no further pressure drop occurs in which a steady state hydrogen concentration prevails.

A preferred embodiment of the invention process is where the anhydride employed is trifluoroacetic anhydride, in the liquid phase, said catalyst is 5 weight percent rhodium on carbon, total catalyst is present in an amount of about 1-10 weight percent and more preferably 5 weight percent, of said anhydride present, said temperature is about 50°-150° C., and said pressure is about 5-15 atmospheres, said atmosphere consisting essentially of hydrogen gas, and said resulting alcohol being 2,2,2-trifluoroethanol.

The following examples are illustrative of the best mode of carrying out the invention as contemplated by us and should not be construed to be limitations on the scope or spirit of the instant invention.

DESCRIPTION OF THE PROCEDURE USED IN EXAMPLES

The following hydrogenation runs were carried out in a thick wall glass reactor attached to a metal pressure line. The line was equipped with a pressure gauge to read from 0-300 psig and connected through a manifold to sources of hydrogen, nitrogen and to a vacuum pump. The volume of the whole system, including the reactor, was 0.206 liter. The contents of the reactor were stirred with a magnetic stirrer. Highest purity trifluoroacetic anhydride, commercially obtained, and commercially available catalysts, were used in all runs. The runs were begun by charging the anhydride and catalyst into the reactor, degasifying the reaction mixture (one freeze-evacuate-thaw cycle) and then admitting hydrogen gas to a desired initial reaction pressure. After testing for leaks, the reactor was immersed in a constant temperature oil bath maintained at a desired constant temperature. The course of the reaction was followed by use of a pressure gauge in which the observed pressure drop resulting from the uptake of hydrogen was monitored throughout the process. The resulting liquid product mixture was analyzed by gas chromatography employing pentafluorobenzene as an internal standard. The results of the runs were reproducible in subsequent runs utilizing the same conditions. No reaction occurred in any of the runs in the absence of catalyst.

EXAMPLE 1

A thick wall glass reactor (volume 50 ml) was charged with 0.1 g of 5% Rh/C catalyst (Strem Chemicals Inc.), 1.9 g of trifluoroacetic anhydride (99+%, Aldrich Chemical Co.) and magnetic stir bar. The reactor was attached to a metal manifold and its contents were degassed by a one-freeze-evacuate-thaw cycle. The reactor was then pressurized with about 10 atm of $H_2$ and immersed in a constant temperature oil bath (113° C.) After three hours, the reactor was cooled down, vented and 1.8 g of liquid product was isolated by vacuum distillation. The product was analyzed by gas chromatography (Porapak QS column) employing pentafluorobenzene as an internal standard. The yield of 2,2,2-trifluoroethanol was 74%.

EXAMPLE 2

The procedure of Example 1 was repeated with the exception that 0.05 g of $Rh_2O_3.5H_2O$ powder and 1.95 g (90 mmols) of $(CF_3CO)_2O$ were charged into the reactor. Within approximately 5 minutes about 80 mmols of hydrogen were consumed; no further consumption occurred within the next hour. The yield of 2,2,2-trifluoroethanol was about 5 weight % and the 2,2,2-trifluoroethyl-2,2,2-trifluoroacetate ester was 39 weight percent.

EXAMPLE 3

The procedure of Example 1 was repeated with the exception that 0.05 g of Ir black (finely divided iridum metal) and 2.0 g of $(CF_3CO)_2O$ were charged into the reactor. After 4½ hrs, 1.7 g of liquid products were isolated. The yield of 2,2,2-trifluoroethanol was 33 weight % and the yield of the 2,2,2-trifluoroethyl-2,2,2-trifluoroacetate was 4 weight percent.

I claim:

1. A process for hydrogenating 2,2,2-trifluoroacetic anhydride to 2,2,2-trifluoroethanol, comprising contacting said anhydride in the liquid phase at a temperature of about 50°-150° C. and pressure of about 5-15 atmospheres with an atmosphere consisting essentially of hydrogen gas, and with a rhodium catalyst, of the group consisting of rhodium metal, rhodium oxides, and mixtures thereof, supported on carbon or alumina.

2. The process of claim 1 wherein said catalyst is selected from the group consists essentially of from about 2 to 10 weight percent rhodium on carbon.

3. The process of claim 2 wherein said catalyst is about 5 weight percent rhodium on carbon.

4. The process of claim 2 wherein said catalyst is present in an amount of about 0.001 to 20 weight percent of said anhydride.

5. The process of claim 4 wherein said catalyst is 5 weight percent rhodium on carbon, present in an amount of about 1–10 weight percent of said anhydride present.

* * * * *